(12) United States Patent
McCauley et al.

(10) Patent No.: US 9,407,047 B1
(45) Date of Patent: Aug. 2, 2016

(54) ELECTRICAL CONNECTOR ASSEMBLY

(71) Applicant: DELPHI TECHNOLOGIES, INC., Troy, MI (US)

(72) Inventors: Kathryn M. McCauley, Durand, MI (US); Charles S. Nelson, Fenton, MI (US)

(73) Assignee: Delphi Technologies Inc., Troy, MI (US)

( * ) Notice: Subject to any disclaimer, the term of this patent is extended or adjusted under 35 U.S.C. 154(b) by 0 days.

(21) Appl. No.: 14/723,669

(22) Filed: May 28, 2015

(51) Int. Cl.
*H01R 13/66* (2006.01)
*H01R 13/502* (2006.01)

(52) U.S. Cl.
CPC .......... *H01R 13/6683* (2013.01); *H01R 13/502* (2013.01)

(58) Field of Classification Search
USPC ................ 439/260, 259, 265, 752, 595, 596; 73/31.05
See application file for complete search history.

(56) References Cited

U.S. PATENT DOCUMENTS

| | | | | |
|---|---|---|---|---|
| 6,244,901 B1 * | 6/2001 | Fujii | ...................... | H01R 4/185 439/595 |
| 6,415,647 B1 * | 7/2002 | Yamada | .............. | G01N 27/4062 204/424 |
| 6,733,326 B2 * | 5/2004 | Lee | ...................... | H01R 12/592 439/495 |
| 6,780,070 B2 * | 8/2004 | Ishikawa | ............ | H01R 13/4362 439/752 |
| 7,004,796 B2 * | 2/2006 | Fukuda | .................. | H01R 43/20 439/752 |
| 7,232,323 B2 * | 6/2007 | Mohs | ..................... | H01R 13/18 439/265 |
| 7,500,875 B2 * | 3/2009 | Lamdiziz | ............ | H01R 13/4223 439/595 |
| 7,563,118 B1 * | 7/2009 | McCauley | ............ | H01R 13/533 439/260 |
| 8,172,624 B2 * | 5/2012 | Tiberio, Jr. | ............. | H01R 13/41 439/733.1 |
| 8,246,368 B2 * | 8/2012 | Buethe | ................. | H01R 13/641 439/259 |
| 9,160,082 B2 * | 10/2015 | Heringhaus | .......... | H01R 13/187 |
| 2002/0177341 A1 * | 11/2002 | Stein, Sr. | ............. | H01R 13/193 439/260 |
| 2003/0024300 A1 * | 2/2003 | Kojima | .............. | G01N 27/4077 73/31.05 |
| 2006/0213254 A1 * | 9/2006 | Satou | .................. | G01N 27/4077 73/31.05 |
| 2007/0272431 A1 * | 11/2007 | Yamauchi | ............ | G01N 27/407 174/138 F |
| 2015/0064950 A1 * | 3/2015 | Wu | ..................... | H01R 13/2407 439/259 |

* cited by examiner

*Primary Examiner* — Alexander Gilman
(74) *Attorney, Agent, or Firm* — Robert J. Meyers (57) ABSTRACT

An electrical connector assembly having a connector body and a conductive terminal disposed within a cavity in the connector body. The terminal is held within the cavity by a rigid stop tab and a flexible lock tab that engage the ends of the connector body. A flexible bias tab having a fixed end attached to the body of the terminal and a free end extending outward laterally from the body of the terminal is configured to engage an inner wall of the cavity and urge the body of the terminal into contact with an opposite inner wall of the cavity, thereby inhibiting lateral movement of the terminal within the cavity. The bias tab may further limit rotational movement of the terminal within the cavity. The bias tab and/or any other feature of the terminal do not engage a locking feature located within the cavity.

8 Claims, 9 Drawing Sheets

ELECTRICAL CONNECTOR ASSEMBLY

TECHNICAL FIELD OF THE INVENTION

The invention relates to electrical connector assemblies, particularly to electrical connector assemblies providing tight lateral positional tolerances of terminals within cavities of connector housings.

BACKGROUND OF THE INVENTION

Conventional sheet metal terminals used with many different electrical connector designs have flexible lock tabs whose function is to retain and/or position the terminal in a cavity of a connector housing that is formed of a dielectric material, such as ceramic or polymer. The terminal is inserted into the cavity by pushing or pulling the terminal into the cavity, during which a free end of the lock tab contacts an inner wall of the cavity and is flexed inwardly, then the free end of the lock tab snaps (suddenly unflexes) into a pocket within the cavity or over a surface on the connector housing outside the cavity. The engagement of the lock tab with the pocket or surface inhibits the terminal from moving in the direction of insertion so that it cannot back out the way it came in. When incorporated with stop features elsewhere in the electrical connector design, the terminal is also inhibited from moving in the insertion direction; and thus becomes longitudinally locked into the connector housing cavity unless the lock tang is purposely depressed (with a screwdriver, for example) to allow removal of the terminal from the housing. While this design locates the terminal longitudinally within the connector housing, the difference in the cross sectional dimensions of the connector housing cavity and the body of the terminal needed to allow insertion of the terminal into the cavity can allow excessive or undesirable lateral positional tolerance of the terminal in the connector body.

The size of electrical connectors continue decrease due to issues of cost, weight, and packaging of the connector. The smaller size of the connector would naturally require tighter manufacturing tolerances to assure proper fit relationship between a terminal and its mating connector cavity. However, to control manufacturing cost, the components in such miniaturized electrical connector designs preferably continue using the conventional fabrication processes and tolerances, such as injection molding or compaction pressing of the connector housing, and stamping and forming the terminal from sheet metal. Therefore, what is desired is a connection system that mimics the effects of tighter manufacturing tolerances while using existing manufacturing processes.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

BRIEF SUMMARY OF THE INVENTION

In accordance with a first embodiment of the invention, an electrical connector assembly is provided. The electrical connector assembly includes a dielectric connector body defining a cavity extending longitudinally therethrough from a connector body first end to an opposed connector body second end and a conductive terminal at least partially disposed within the cavity and longitudinally oriented within the cavity. The terminal defines a rigid stop tab that extends laterally from a body of the terminal. The stop tab is configured to engage the first end of the connector body, thereby inhibiting longitudinal movement of the terminal within the cavity in a first longitudinal direction. The terminal also defines a flexible lock tab having a fixed end that is attached to the body of the terminal and a free end that extends outward laterally from the body of the terminal. The lock tab is configured to flex inwardly when contacting a first inner cavity wall of the cavity and configured to flex outwardly when the stop tab engages the first end of the connector body, thereby engaging the second end of the connector body and inhibiting longitudinal movement of the terminal within the cavity in a second longitudinal direction that is opposite the first longitudinal direction. The terminal further defines a flexible bias tab having a fixed end attached to the body of the terminal and a free end extending outward laterally from the body of the terminal. The bias tab is configured to engage a second inner wall of the cavity and urge the body of the terminal into contact with a third inner wall of the cavity that is opposite the second inner wall, thereby inhibiting lateral movement of the terminal within the cavity.

In accordance with a second embodiment of the invention, the bias tab does not engage a locking feature within the cavity.

In accordance with a third embodiment of the invention, the terminal does not engage a locking feature within the cavity.

In accordance with a fourth embodiment of the invention, a bias tab width is at least 50% of a second inner wall width, thereby inhibiting rotational movement of the terminal within the cavity.

In accordance with a fifth embodiment of the invention, the terminal includes a second flexible bias tab having a fixed end attached to the body of the terminal and a free end extending outward laterally from the body of the terminal. The bias tab and the second bias tab are configured to engage two adjacent inner walls of the cavity and urge the body of the terminal into contact with two other inner walls of the cavity opposite the two adjacent inner walls, thereby further inhibiting lateral movement of the terminal within the cavity.

In accordance with a sixth embodiment of the invention, the terminal defines a flexible contact tab configured to engage a mating contact feature of a mating electrical connector assembly.

In accordance with a seventh embodiment of the invention, the connector body defines a plurality of cavities extending longitudinally therethrough from the first end to the opposed second end. The electrical connector assembly comprises a plurality of terminals as described above. One terminal of the plurality of terminals is disposed within each cavity of the plurality of cavities. The bias tab of each terminal in the plurality of terminals engages a distal inner wall of each cavity in the plurality of cavities and urges each terminal in the plurality of terminals toward a mesial inner wall of each cavity in the plurality of cavities.

In accordance with an eighth embodiment of the invention, an electrical assembly is provided. The electrical assembly includes a circuit board substrate having a mating electrical connector assembly defining a plurality of mating contact features and an electrical connector assembly as described above. The contact tabs of the plurality of terminals of the electrical connector assembly engage the plurality of mating contact features of the circuit board substrate, thus establishing an electrical connection between the circuit board substrate and the electrical connector assembly. The circuit board substrate may include an internal combustion exhaust sensor.

BRIEF DESCRIPTION OF THE SEVERAL VIEWS OF THE DRAWING

The present invention will now be described, by way of example with reference to the accompanying drawings, in which.

DETAILED DESCRIPTION OF THE INVENTION

Presented herein is an electrical connector assembly that provides reduced lateral positional tolerance over similar prior art connector designs. Besides the lock tab and the stop features of the terminal described in the background of the invention, the terminal includes a bias tab that protrudes from the connector body and contacts an inner wall of the connector housing cavity, forcing the connector body against the opposite inner wall of the cavity, thus inhibiting movement of the terminal within the cavity and limiting the lateral positional tolerance of the terminal in the connector housing in at least one of the lateral directions. If the width of the bias tab is sufficiently wide in relation to the width of the cavity inner wall, the bias tab may also inhibit rotational movement of the terminal within the cavity. This electrical connector may be produced using the same manufacturing methods (e.g. stamping, forming, molding) as prior art electrical connector assemblies providing an electrical connector assembly with tighter terminal location tolerances and comparable manufacturing costs compared to similar prior art electrical connector assemblies.

Figure 1:
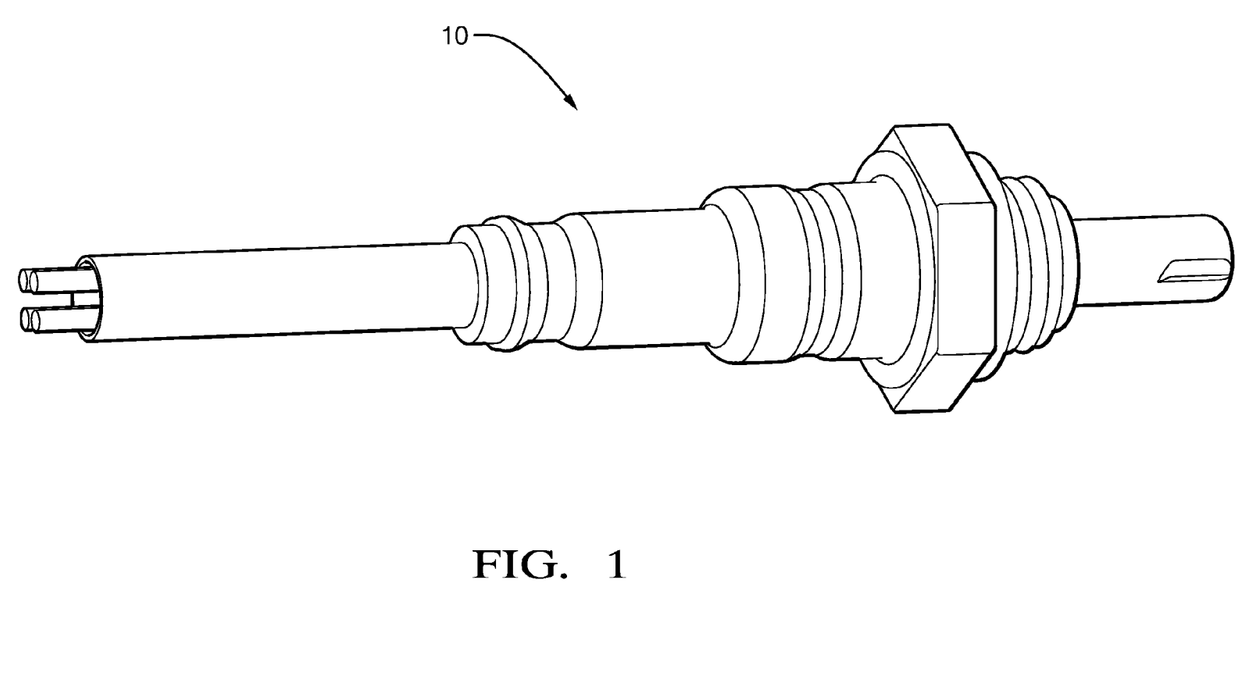
FIG. 1 is a perspective view of an automotive internal combustion exhaust sensor according to one embodiment.
Figure 2:
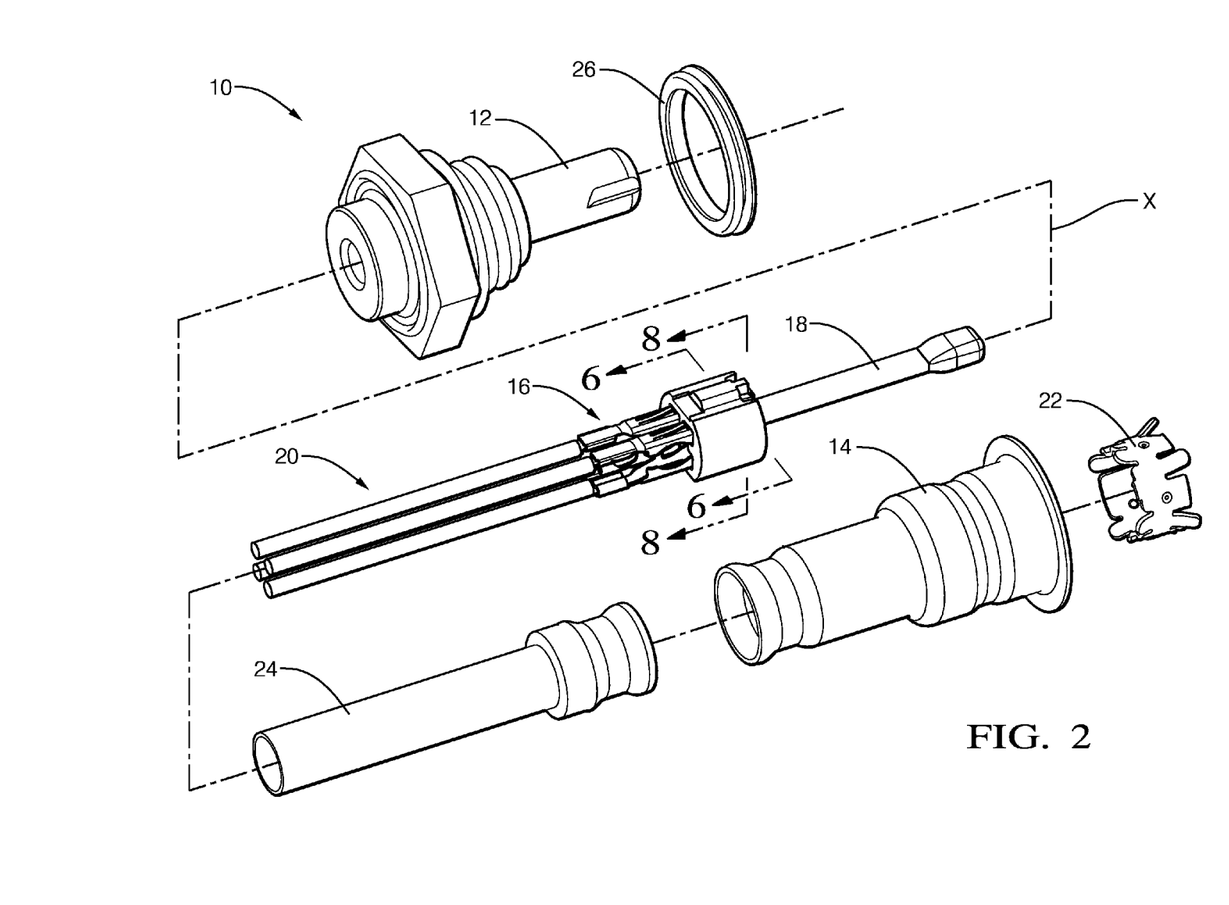
FIG. 2 is an exploded perspective view of the automotive internal combustion exhaust sensor of FIG. 1 including an electrical connector assembly according to one embodiment.

FIG. 1 illustrates a non-limiting example of an application of electrical connector assembly used in an electrical assembly, in this example an automotive internal combustion exhaust sensor 10. As shown in FIG. 2, the internal combustion exhaust sensor includes a front and rear housing 12, 14, an electrical connector assembly 16 configured to interconnect a circuit board substrate 18 containing the internal combustion exhaust sensor circuitry to a number of wire cables 20, a clip 22 configured to secure the electrical connector assembly 16 within the rear housing 14, a protective sleeve 24 to protect the wire cables 20, and a gasket 26 for mounting the front housing 12.

Figure 3:
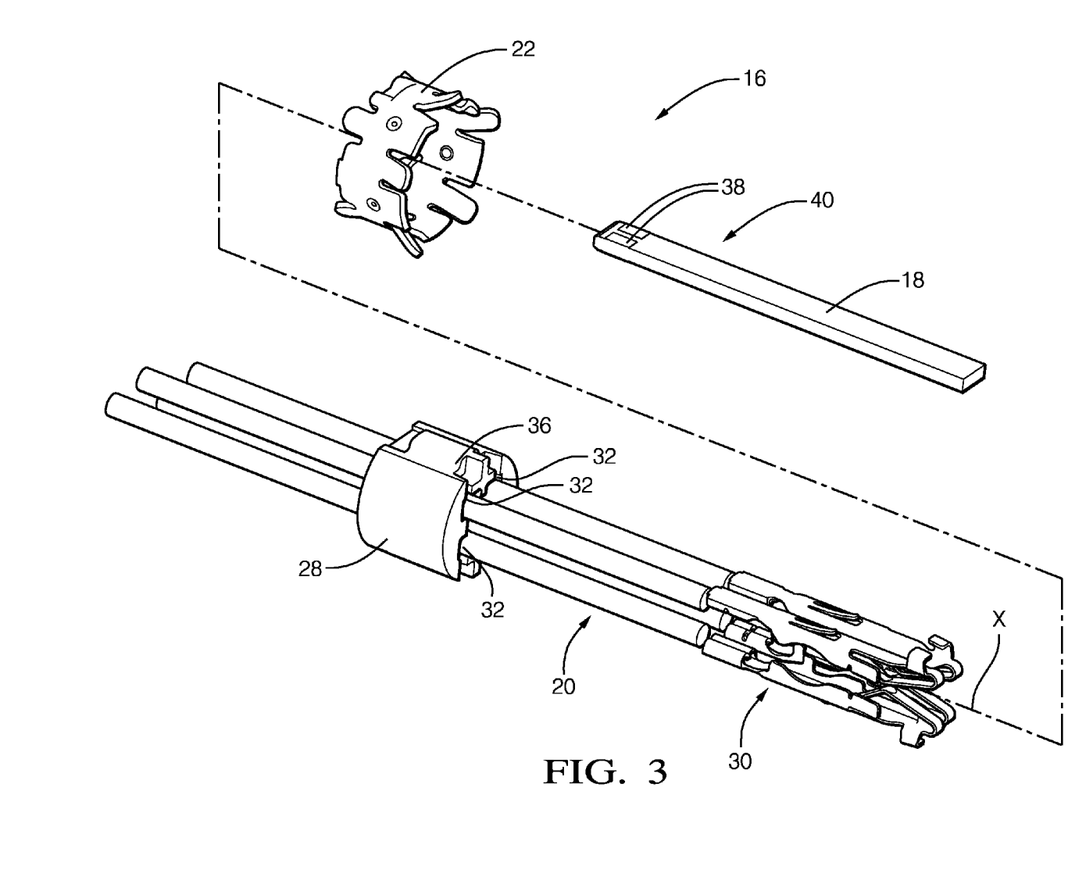
FIG. 3. is an exploded perspective view of the electrical connector assembly shown in FIG. 2 according of one embodiment.
Figure 4:
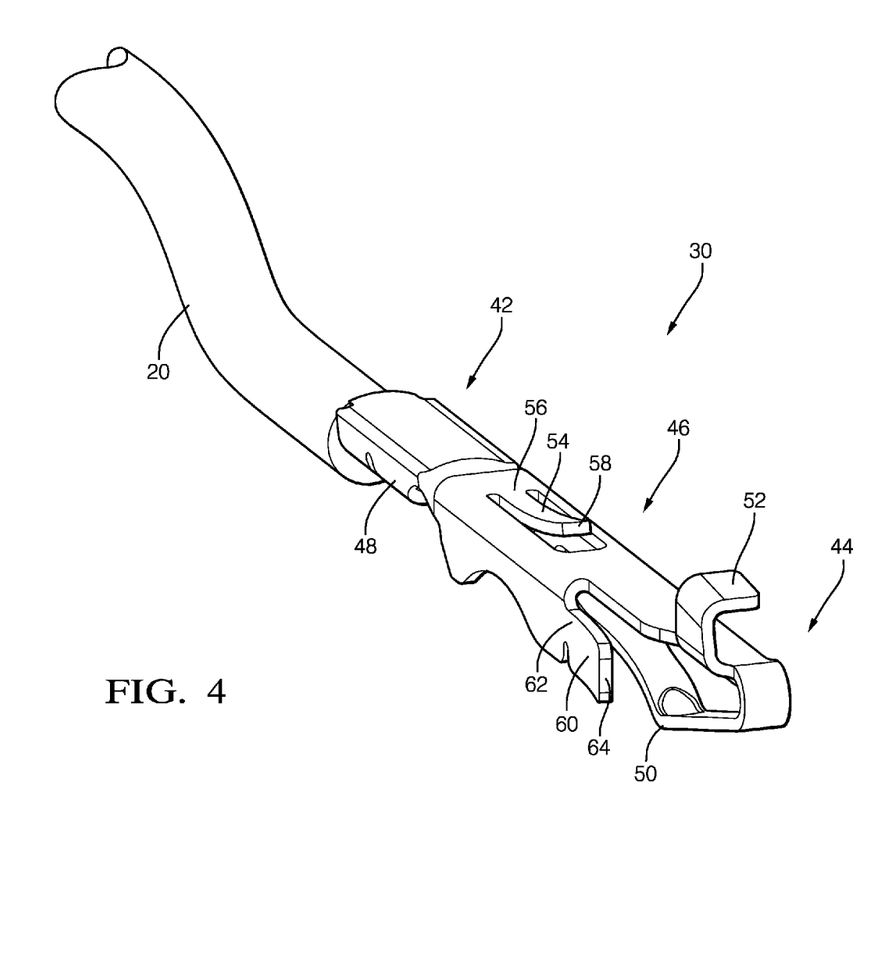
FIG. 4 is a perspective view of a terminal of the electrical connector assembly of FIG. 3 according to one embodiment.

The details of the electrical connector assembly 16, hereinafter referred to as the connector 16 are shown in FIGS. 3 and 4. The connector 16 is made up of an insulative connector body 28 and at least one electrically conductive terminal 30 that, when fully assembled, is at least partially disposed within a cavity 32 defined by the connector body 28. The cavity 32 is defined along a longitudinal axis X and extends from an opening 34 in a front surface 36 of the connector body 28 through to another opening in a rear surface (not shown due to perspective) of the connector body 28. According to the illustrated embodiment, the connector body 28 has four cavities 32 with a generally square cross section. Other embodiments with cavities having more or fewer cavities with generally rectangular, triangular, or round cross sections may also be envisioned.

The connector body 28 is formed of a dielectric material, such as a polymeric or ceramic material. The choice of material will be primarily dependent on the intended application of the connector 16. The connector body 28 may be formed by molding the material into the desired shape. The design and fabrication of connector bodies of this type are well known to those skilled in the art.

As illustrated in FIG. 4, the terminal 30 is attached to an end of the wire cable 20, hereinafter the cable 20, and is configured to electrically interconnect to a mating terminal 38 of a mating electrical connector assembly 40. The terminal 30 is made up of an attachment portion 42, a connection portion 44, and a body portion 46.

The attachment portion 42 is configured to attach the terminal 30 to the cable 20. In the illustrated embodiment, the attachment portion 42 comprises a pair of crimping wings 48 that are folded and crimped to the cable 20. Other embodiments of the terminal 30 may be envisioned, for example in which the attachment portion 42 comprises a tubular section that is crimped or soldered to the cable 20 or a planar section to which the cable 20 is sonically welded. Other attachment means known to those skilled in the art may also be used for the attachment portion 42.

The connection portion 44 of the illustrated embodiment is a flexible member defining a generally triangular shape. The apex of the connection portion 44 defines a flexible contact tab 50 configured to contact the mating terminal 38 and flex the connection portion 44 to apply a normal force to the mating terminal 38 in order to provide a reliable electrical connection there between. Other embodiments of the terminal may be envisioned in which the connection portion is a male blade, a female socket, or another type of connection portion known to those skilled in the art.

The body portion 46 of the terminal 30 is located intermediate the attachment portion 42 and the connection portion 44 and interconnects the two portions and has a generally square cross section. The body portion 46 defines a rigid stop tab 52 that extends laterally from one end of the body portion 46. As used herein, the lateral direction Y is substantially orthogonal to the longitudinal direction X, i.e. ±10° of absolutely orthogonal. Further, as used herein "rigid" means that the stop tab 52 is not deformed when subjected to forces typically experienced in the normal application of the terminal 30 and is plastically deformed when subjected to forces greater than those typically experienced in the normal application of the terminal 30. The body portion 46 also defines a flexible lock tab 54 on the other end of the body portion 46 that has a fixed end 56 attached to the body portion 46 and a free end 58 extending laterally outwardly, or away, from the body portion 46. The body portion 46 further defines a flexible bias tab 60 located intermediate the stop tab 52 and the lock tab 54. As used herein "flexible" means that the lock tab 54 and/or the bias tab 60 is elastically deformed when subjected to forces typically experienced in this application of the terminal 30. The bias tab 60 also has a fixed end 62 attached to the body portion 46 and a free end 64 extending laterally outwardly, or away, from the body portion 46.

The terminal 30 may be formed from a tin plated copper sheet or stainless steel and the attachment portion 42, connection portion 44, body portion 46, stop tab 52, lock tab 54, and bias tab 60 may all be formed by a stamping and folding process. Other manufacturing process known to those skilled in the art may also be used to form the terminal 30.

Figure 5:
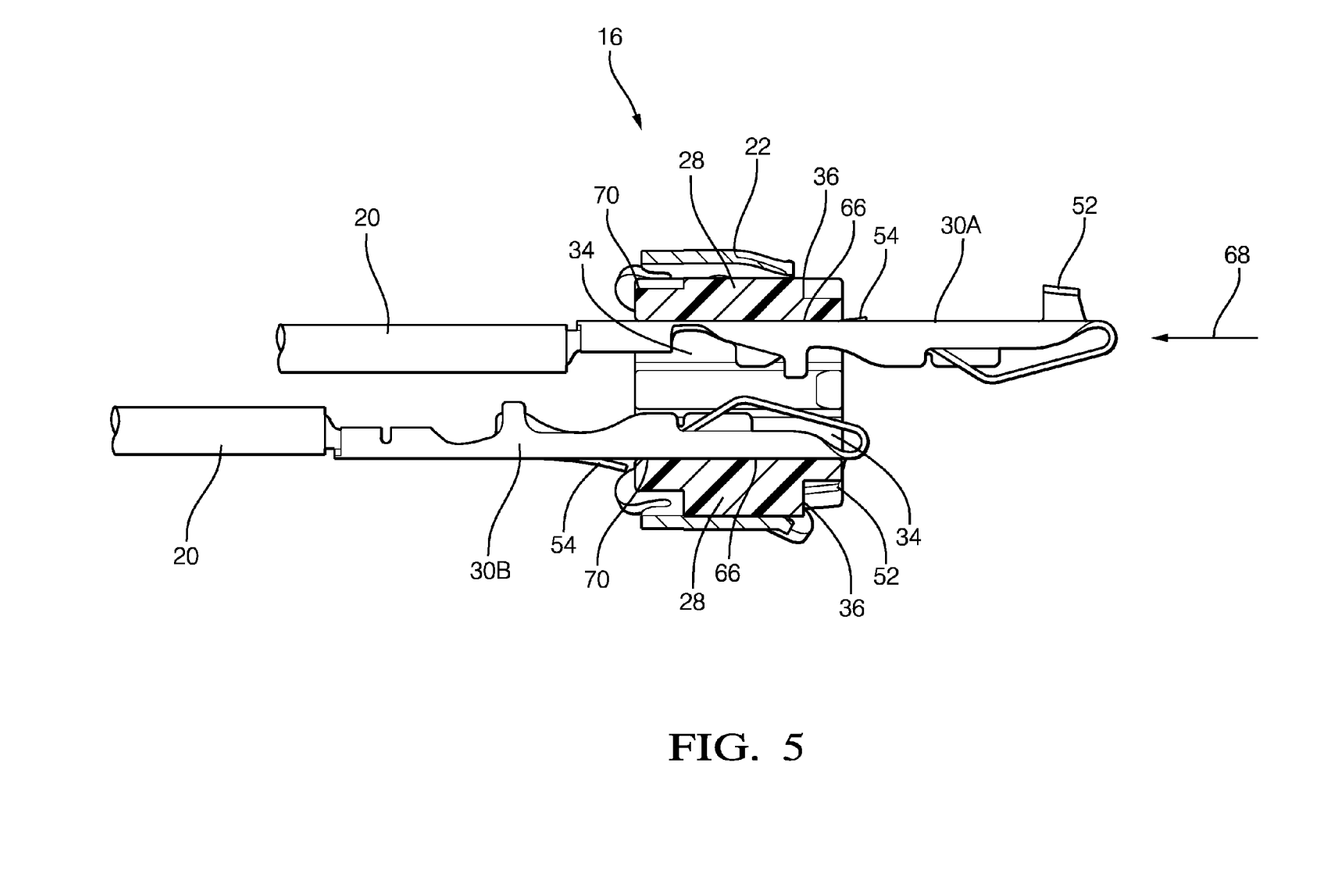
FIG. 5 is a cross sectional view of the electrical connector assembly of FIG. 3 along the plane A-A showing one terminal partially inserted into the connector housing and another terminal fully inserted according to one embodiment.
Figure 7:
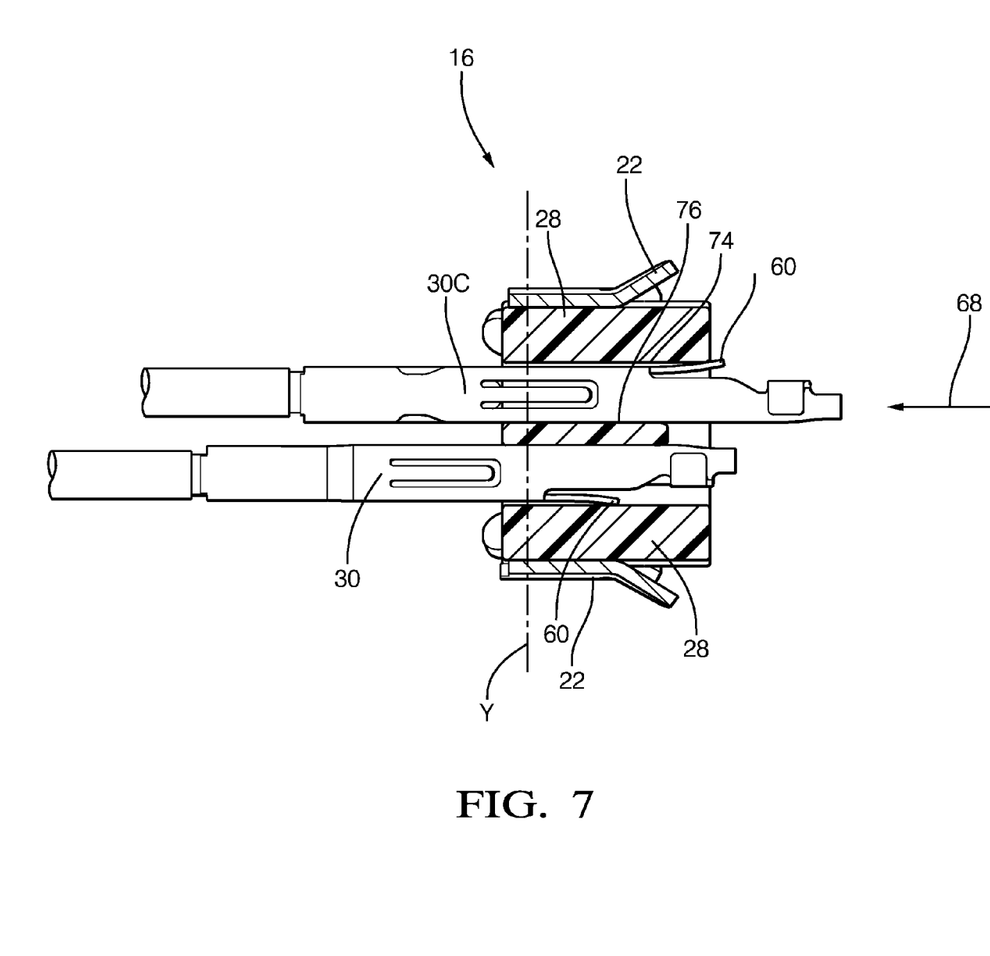
FIG. 7 is a cross sectional view of the electrical connector assembly of FIG. 3 along the plane B-B showing one terminal partially inserted into the connector housing and another terminal fully inserted according to one embodiment.

FIGS. 5 and 7 illustrate a non-limiting process of inserting the terminal 30 within the connector body 28. As shown in FIG. 5 the attachment portion 42 of the terminal 30 is inserted into the opening 34 in the front surface 36 of the connector body 28. As the terminal 30 is pushed through the cavity 32, the free end 58 of the lock tab 54 engages a first inner cavity wall 66 and flexes inwardly toward the body portion 46 as seen with the upper terminal 30A. As used herein, "inwardly" means that the free end 58 moves in a substantially lateral direction toward the longitudinal axis of the terminal 30.

The terminal 30 is inserted into the cavity 32 until the stop tab 52 engages the front surface 36 of the connector body 28 inhibiting further longitudinal movement of the terminal 30 in the insertion direction 68. The lock tab 54 is located on the body portion 46 so that when the stop tab 52 engages the front surface 36, the free end 58 of the lock tab 54 is out of the cavity 32 and no longer engaging the first inner cavity wall 66 as seen with the lower terminal 30B. The free end 58 of the lock tab 54 then springs outwardly and engages the rear surface 70 of the connector body 28 inhibiting further longitudinal movement of the terminal 30 in the direction opposite 72 of the insertion direction 68, thereby inhibiting longitudinal movement of the terminal 30 within the cavity 32. As used herein, "outwardly" means that the free end 58 moves in a substantially lateral direction away from the longitudinal axis of the terminal 30.

As shown in FIG. 7, as the upper terminal 30C is inserted into the cavity 32, the free end 64 of the bias tab 60 engages a second inner cavity wall 74 and urges the terminal 30 into contact with a third inner cavity wall 76 that is opposite the second inner cavity wall 74, thereby inhibiting lateral movement of the terminal 30 within the cavity 32 as seen. The first inner cavity wall 66 and the second inner cavity wall 74 may be different inner cavity walls or they may be the same inner cavity wall.

As illustrated in FIGS. 5-8, the bias tab 60 does not engage any locking feature that protrudes from an inner wall within the cavity 32 nor does any other feature of the terminal 30 engage a locking feature within the cavity 32.

According to the illustrated embodiment, the width of the bias tab 60 width is over 50% of the width of the second inner cavity wall 74. Without subscribing to any particular theory of operation, this width of the bias tab 60 inhibits rotational movement of the terminal 30 within the cavity 32. Other embodiments of the terminal may be envisioned having a pair of bias tabs located on the edges of the terminal that would cooperate to inhibit rotational movement of the terminal within the cavity.

Figure 9:
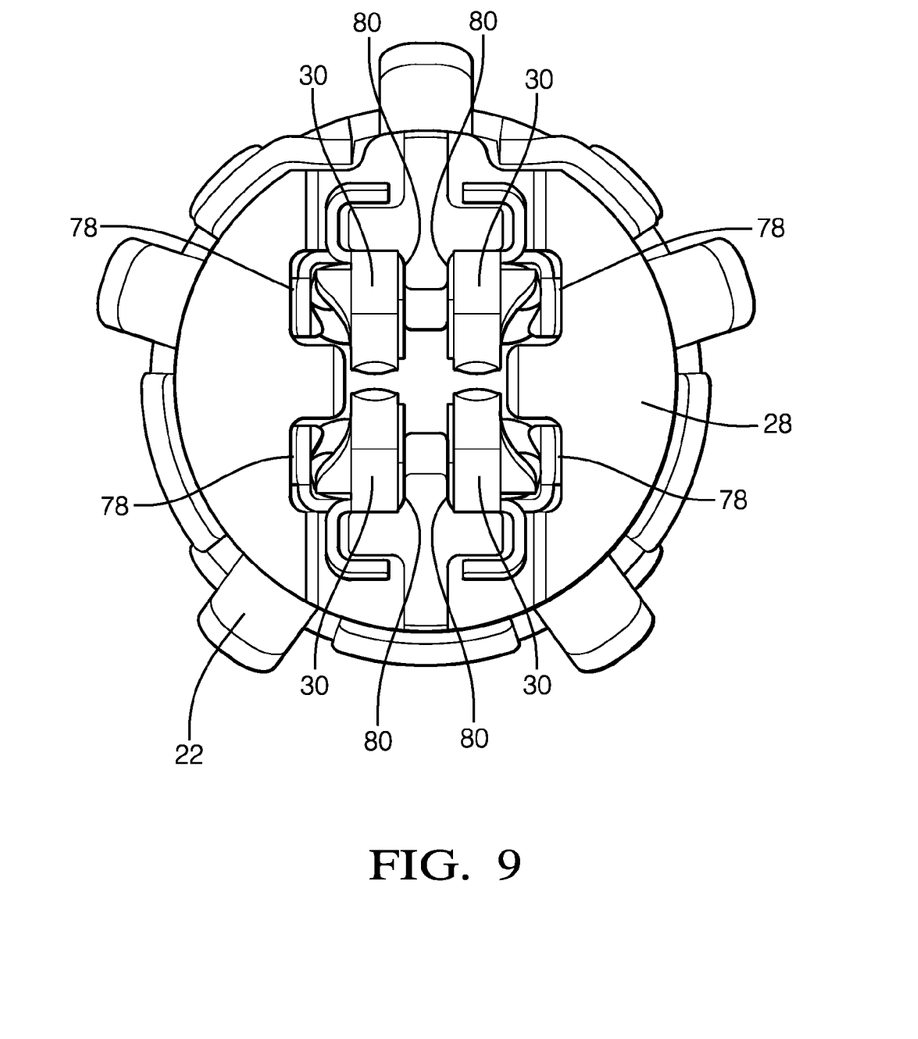
FIG. 9 is an end view of the electrical connector assembly of FIG. 3 according to one embodiment.

As illustrated in FIG. 9, the terminals 30 are arranged in the cavities 32 of the connector body 28 such that the bias tab 60 of each one of the terminals 30 engages a distal inner cavity wall 78 of each cavity 32 and urges each of the terminals 30 toward a mesial inner cavity wall 80 of each cavity 32. As used herein, "distal inner wall" refers to the inner wall of the cavity 32 that is farthest from the central longitudinal axis X of the connector body 28 and "mesial inner wall" refers to the inner wall of the cavity 32 that is closest to the central longitudinal axis X of the connector body 28. This provides the benefit of minimizing the lateral distance between the contact tabs 50 of each of the terminals 30 which further minimizes the distance between the corresponding mating terminals 38. This allows a smaller mating electrical connector assembly 40 to be used with this connector 16.

Figure 6:
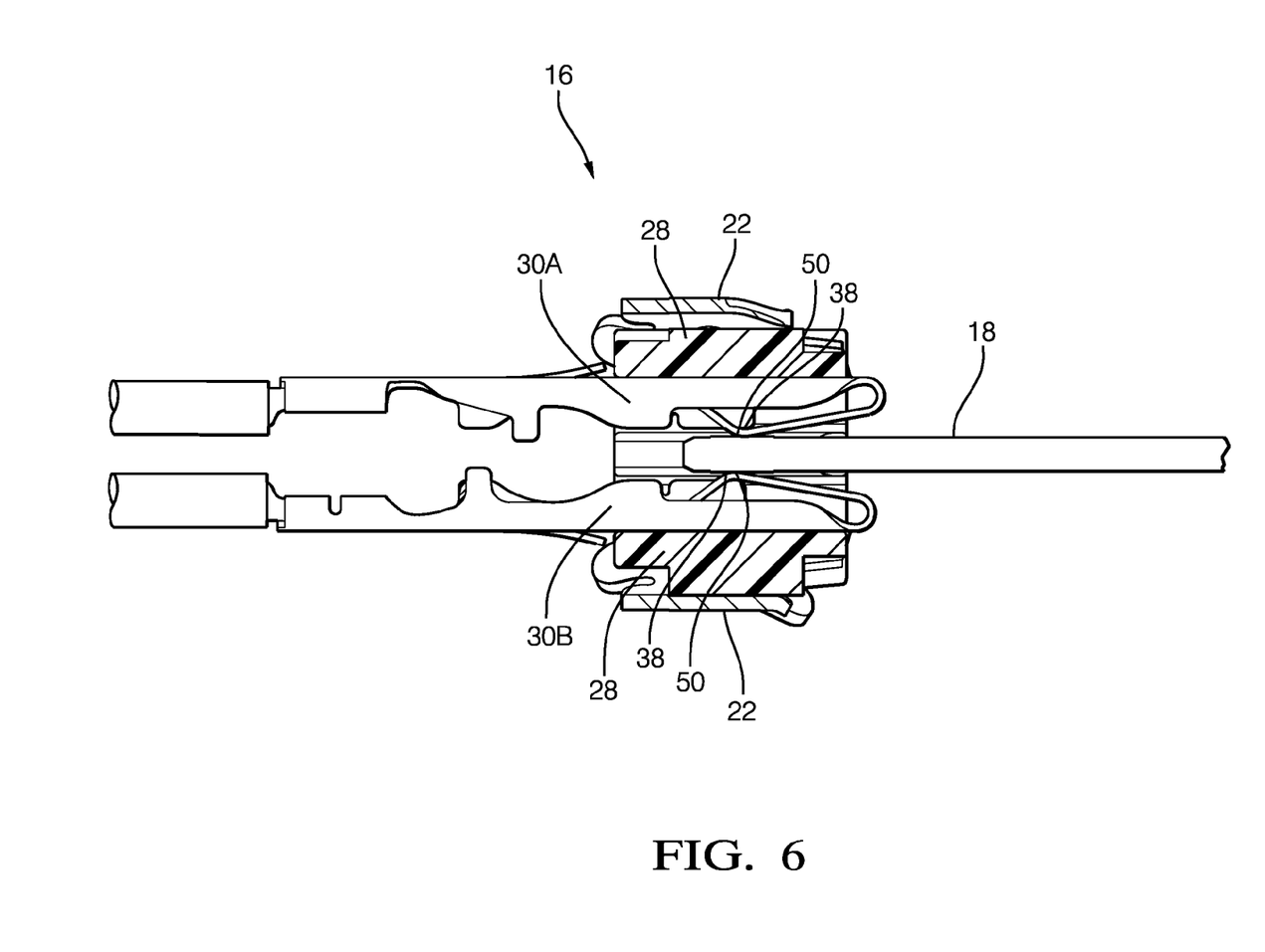
FIG. 6 is a cross sectional view of the electrical connector assembly of FIG. 3 along the plane A-A showing two terminals fully inserted into the connector housing and a circuit board substrate engaging the terminals according to one embodiment.
Figure 8:
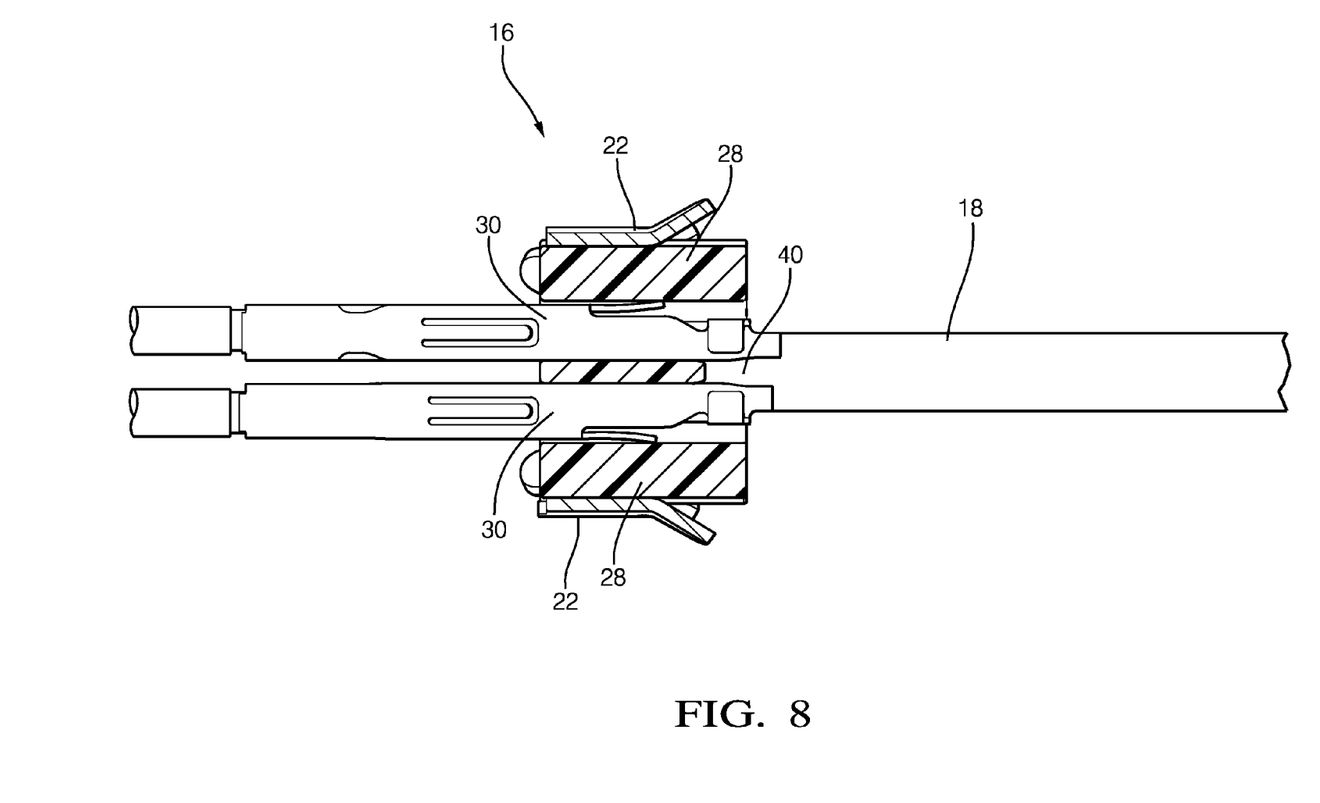
FIG. 8 is a cross sectional view of the electrical connector assembly of FIG. 3 along the plane B-B showing two terminals fully inserted into the connector housing and a circuit board substrate engaging the terminals according to one embodiment.

The circuit board substrate 18 is formed of a ceramic material to accommodate the thermal environment to which the internal combustion exhaust sensor is subjected. Alternative electrical assemblies may use circuit board substrates formed of epoxy or polyimide resins. The resin may be reinforced with a woven glass cloth or other matrix such as chopped fibers. Substrates formed of such materials are typically ceramic or FR-4 or G-10 type circuit boards. The substrate may alternatively be constructed of rigid polymer materials. This listing of acceptable substrate materials is not exhaustive and other materials may also be used successfully. The materials and manufacturing techniques used to form circuit board substrates are well known to those skilled in the art. The circuit board substrate 18 defines a mating electrical connector assembly 40 with mating terminals 38 formed of conductive pads deposited near the edge of the circuit board substrate 18 that are configured to align with the contact tabs 50 of the connector 16 when the circuit board substrate 18 in fully inserted into the connector body 28 of the connector 16 as shown in FIGS. 6 and 8.

In alternative embodiments of the connector, the terminal may include a second flexible bias tab (not shown). The bias tab and the second bias tab are configured to engage two adjacent inner walls of the cavity and urge the body of the terminal into contact with two other inner walls of the cavity opposite the two adjacent inner walls, thereby further inhibiting lateral movement of the terminal within the cavity.

Accordingly an electrical connector assembly 16 is provided. The bias tabs 60 defined by the terminals 30 urge the body portions 46 of the terminals 30 into contact with the inner walls of the cavities 32, thereby limiting lateral movement of the terminal 30 within the cavity 32 and decreasing the lateral positional tolerance required for the connector 16. This allows more precise lateral positioning of the terminals 30 which can successfully be used with smaller mating connector assemblies, such as the conductive pads on the edge of the circuit board substrate 18. The width of the bias tab 60 also is configured to limit rotational movement of the terminal 30 within the cavity 32. The inner walls of the cavities 32 do not define any lock features, thus simplifying the design and fabrication of the connector body 28 and reducing manufacturing cost.

While the connector 16 illustrated herein is applied to interconnect a ceramic circuit board substrate 18 in an automotive internal combustion exhaust sensor 10, many other embodiments of the invention may be envisioned for many other applications of the connector.

While this invention has been described in terms of the preferred embodiments thereof, it is not intended to be so limited, but rather only to the extent set forth in the claims that follow. Moreover, the use of the terms first, second, etc. does not denote any order of importance, but rather the terms first, second, etc. are used to distinguish one element from another. Furthermore, the use of the terms a, an, etc. do not denote a limitation of quantity, but rather denote the presence of at least one of the referenced items.

We claim:

1. An electrical connector assembly, comprising:
   a connector body defining a cavity extending longitudinally therethrough from a connector body first end to an opposed connector body second end; and
   a terminal at least partially disposed within the cavity and longitudinally oriented within the cavity, said terminal comprising:
   a rigid stop tab extending laterally from a terminal body and configured to engage the first end,
   a flexible lock tab having a fixed end attached to the terminal body and a free end extending outward laterally from the terminal body and configured to flex inwardly when contacting a first cavity wall and configured to flex outwardly when the stop tab engages the first end, and
   a flexible bias tab having a fixed end attached to the body of the terminal and a free end extending outward laterally from the terminal body and configured to engage a second cavity wall and urge the terminal body into contact with a third cavity wall opposite the second cavity wall.

2. The electrical connector assembly according to claim 1, wherein the bias tab does not engage a locking feature within the cavity.

3. The electrical connector assembly according to claim 1, wherein the terminal does not engage a locking feature within the cavity.

4. The electrical connector assembly according to claim 1, wherein a bias tab width is at least 50% of a second cavity wall width, thereby inhibiting rotational movement of the terminal within the cavity.

5. The electrical connector assembly according to claim 1, wherein the terminal defines a flexible contact tab configured to engage a mating contact feature of a mating electrical connector assembly.

6. The electrical connector assembly according to claim 5, wherein the connector body defines a plurality of cavities extending longitudinally therethrough from the first end to the second end, wherein the electrical connector assembly comprises a plurality of terminals according to claim 5, wherein one terminal of the plurality of terminals is disposed within each cavity of the plurality of cavities, and wherein the bias tab of each terminal in the plurality of terminals engages a distal inner wall of each cavity in the plurality of cavities and urges each terminal in the plurality of terminals toward a mesial inner wall of each cavity in the plurality of cavities.

7. An electrical assembly, comprising:
   a circuit board substrate having a mating electrical connector assembly defining a plurality of mating contact features; and
   the electrical connector assembly according to claim 6, wherein the contact tabs of the plurality of terminals engage the plurality of mating contact features.

8. The electrical assembly according to claim 7, further comprising an internal combustion exhaust sensor.

* * * * *